United States Patent
Xu et al.

(10) Patent No.: US 7,056,544 B2
(45) Date of Patent: Jun. 6, 2006

(54) METHODS FOR PRODUCING POTATO PRODUCTS

(75) Inventors: Feng Xu, Davis, CA (US); Lene Venke Kofod, Uggelose (DK); Hans Sejr Olsen, Holte (DK)

(73) Assignees: Novozymes, Inc., Davis, CA (US); Novozymes A/S, Bagsvaerd (DK)

( * ) Notice: Subject to any disclaimer, the term of this patent is extended or adjusted under 35 U.S.C. 154(b) by 476 days.

(21) Appl. No.: 09/834,560

(22) Filed: Apr. 13, 2001

(65) Prior Publication Data

US 2002/0004085 A1    Jan. 10, 2002

Related U.S. Application Data

(63) Continuation-in-part of application No. 09/704,395, filed on Nov. 1, 2000, now abandoned.

(30) Foreign Application Priority Data

Apr. 14, 2000    (DK) ............................... 2000 00623

(51) Int. Cl.
   *A23L 1/216*    (2006.01)
(52) U.S. Cl. ........................................ 426/52; 426/637
(58) Field of Classification Search .................. 426/50, 426/52, 102, 302, 438, 441, 637, 808
   See application file for complete search history.

(56) References Cited

U.S. PATENT DOCUMENTS

| | | | | |
|---|---|---|---|---|
| 4,058,631 | A | | 11/1977 | Roan ........................... 426/438 |
| 4,503,127 | A | | 3/1985 | Fan et al. .................... 426/438 |
| 5,312,631 | A | * | 5/1994 | Yamashita .................... 426/52 |
| 5,897,898 | A | * | 4/1999 | Rogols et al. .............. 426/102 |
| 5,965,189 | A | * | 10/1999 | Stevens et al. ......... 426/102 X |
| 6,033,697 | A | * | 3/2000 | Judkins et al. .............. 426/102 |
| 6,524,639 | B1 | * | 2/2003 | Rogols et al. .............. 426/637 |

* cited by examiner

*Primary Examiner*—Arthur L. Corbin

(74) *Attorney, Agent, or Firm*—Robert L. Starnes

(57) ABSTRACT

The present invention relates to methods for producing consumable products from potatoes, comprising: (a) treating a potato substance with an effective amount of one or more exogenous enzymes selected from the group consisting of an amyloglucosidase, glucose oxidase, laccase, lipase, maltogenic amylase, pectinase, pentosanase, protease, and transglutaminase, and (b) processing the enzyme-treated potato substance to produce a potato product. The invention also relates to consumable products obtained from potatoes by the methods of the present invention.

22 Claims, No Drawings

METHODS FOR PRODUCING POTATO PRODUCTS

CROSS-REFERENCE TO RELATED APPLICATIONS

This application is a continuation-in-part of U.S. application Ser. No. 09/704,395 filed on Nov. 1, 2000, now abandoned, and DK application Ser. No. PA 2000 00623 filed on Apr. 14, 2000, which applications are fully incorporated herein by reference.

BACKGROUND OF THE INVENTION

1. Field of the Invention

The present invention relates to methods for producing consumable products from potatoes.

2. Description of the Related Art

Potato foods are consumed worldwide where fried potato products are particularly favored, especially French fries and potato chips. However, consumer concerns regarding fat intake have resulted in baked potato products.

Methods for making fried potato products directly from potatoes involve some combination of the following basic steps: (1) peeling, (2) slicing, (3) washing, (4) frying in edible oils, and (5) seasoning. Similar methods for producing baked potato products are used except the frying step is replaced with a baking step.

For example, the preparation of French fries generally comprises peeling, cutting, blanching, and frying. Other treatment steps are often included such as preheating, sugar-coating, drying, partial frying, or freezing. The preheating step is proposed to activate endogenous pectin methyl esterase to strengthen cell walls, leading to smoother cutting. The sugar-coating step enhances the golden colour-forming Maillard reaction during frying. Moreover, manufacturers often add different, proprietary steps of a physical-chemical nature to achieve various desirable qualities of the final products.

French fries, served by fast food restaurants and food services, are commonly purchased in bulk from commercial suppliers in the form of partially fried (par-fried) potato strips which are stored frozen until ready for consumption. The par-fried potato strips are prepared for consumption by, for example, frying in fat or oil.

The properties of potato foods such as French fries and potato chips differ, for example, depending on the degree of crispiness and colour desired. For instance, crispiness and a golden colour are often desirable for French fries, whereas a pale-yellow colour is mere suitable for potato chips. Various processing methods have been developed for optimizing these properties.

U.S. Pat. No. 4,058,631 discloses the pretreatment of raw, starchy food products with an aqueous solution of alpha-amylase to reduce the absorption of fats and oils during frying.

U.S. Pat. No. 4,503,127 discloses a hot oil pre-treatment method for activating pectin methylesterase endogenous to starch-containing vegetables in order to lower the fat content of the final potato product.

GB 1,278,736 discloses the use of alpha-amylase to reduce the viscosity of a potato-water mixture.

It is an object of the present invention to provide improved methods for producing consumable products from potatoes.

SUMMARY OF THE INVENTION

The present invention relates to methods for producing consumable products from potatoes, comprising: (a) treating a potato substance with an effective amount of one or more exogenous enzymes selected from the group consisting of an amyloglucosidase, glucose oxidase, laccase, lipase, maltogenic amylase, pectinase, pentosanase, protease, and transglutaminase, and (b) processing the enzyme-treated potato substance to produce a potato product.

The invention also relates to consumable products obtained from potatoes by the methods of the present invention.

DETAILED DESCRIPTION OF THE INVENTION

The present invention relates to methods for producing a consumable product from potatoes, comprising: (a) treating a potato substance with an effective amount of one or more exogenous enzymes selected from the group consisting of an amyloglucosidase, glucose oxidase, laccase, lipase, maltogenic amylase, pectinase, pentosanase, protease, and transglutaminase, and (b) processing the enzyme-treated potato substance to produce a potato product, wherein one or more properties of the potato product resulting from the enzyme treatment are improved relative to a potato product without enzyme treatment.

The methods of the present invention are advantageous over conventional methods in that the methods provide novel properties of taste, texture, appearance, and fat content of the potato product. Moreover, the methods of the present invention are more efficient for producing potato products with respect to energy use and time.

In the methods of the present invention, the potato substance may by any material comprising a variety of a potato. The potato substance may simply be farm-grown potatoes (raw potatoes) of any variety. Such varieties include, but are not limited to, Bintje, Russet Burbank, Kennebec, Norchip, Atlantic, Shepody, Sebago, Red Pontiac, Red Warba, Irish Cobbler "BC", Norgold Russet "BC", Norland, Atlantic, White Rose, Superior, Centennial Russet, Keswick "NB 1", and Green Mountain.

The potatoes are typically washed, peeled, and cut into slices or strips of a desired size and shape or any other form or shape for that matter. For example, French fries may be in the shape of shoe-string, crinkle-cut, and thick straight-cut strips. The strips may have a width and thickness of from about 5 mm to about 15 mm and several cm's in length. After cutting, the strips may be washed to remove extracellular surface starch to prevent the slices from sticking together during cooking.

The potato substance may also be a potato batter or potato dough, which is subsequently formed into a desired shape.

The potato product may be any fried, baked, or cooked product obtained from potatoes, which is ready for consumption. Alternatively, the potato product may be a frozen product, which is to be sold as such with the intention that the product subsequently is made ready for consumption by frying, baking, or microwaving. The potato products obtained by the methods of the present invention include, but are not limited to, French fries, potato chips, potato sticks, potato pancakes, tater tots, hash browns, home fries, baked potatoes, and potato balls for salad.

The term "improved property" is defined herein as any property of a potato product, which is altered by the action of the one or more enzymes relative to a potato product in which the potato substance is not treated with enzyme to render the enzyme-treated product more desirable for consumption. The improved property may include, but is not limited to, increased crispiness, colour enhancing effect, colour fading effect, increased stiffness, rugged appearance, improved fried flavour, and lower fat content.

The improved property may be determined by comparison of potato products prepared from a potato substance treated with and without an enzyme(s) in accordance with the methods of the present invention. Techniques for determining such improved properties achieved by use of the instant methods are described herein. Organoleptic qualities may be evaluated using procedures well established in the food industry, and may include, for example, the use of a panel of trained taste-testers.

The term "increased crispiness" is defined herein as an increase in the crunchiness of the consumable potato product obtained from a potato substance treated with enzyme relative to the untreated potato product.

The term "colour enhancing effect" is defined herein as an increase in golden brown or brown colour of the consumable potato product obtained from a potato substance treated with enzyme relative to the untreated potato product.

The term "colour fading effect" is defined herein as a decrease in golden brown or brown colour of the consumable potato product obtained from a potato substance treated with enzyme relative to the untreated potato product. Preferably, the colour is a light yellow colour.

The term "increased stiffness" is defined herein as an increase in the firmness of the outer coat of the consumable potato product obtained from a potato substance treated with enzyme relative to the untreated potato product.

The term "rugged appearance" is defined herein as a pebbled surface of the consumable potato product obtained from a potato substance treated with enzyme, which is absent in the untreated potato product.

The term "improved flavour" is defined herein as a consumable potato product, obtained from a potato substance treated with enzyme, having a "fried" flavour when evaluated by a trained test panel, which is absent in the untreated potato product.

The term "lower fat content" is defined herein as a consumable potato product, obtained from a potato substance treated with enzyme, having a lower fat content compared to an untreated potato product.

In a preferred embodiment, the one or more enzymes improve one or more properties of the potato product obtained.

In a more preferred embodiment, the improved property is increased crispiness of the potato product. In another preferred embodiment, the potato product resulting from enzyme-treatment remains crispy for an extended period of time compared to a potato product obtained without the enzyme treatment.

In another more preferred embodiment, the improved property is a colour enhancing effect, i.e., a golden brown or brown colour of the potato product.

In another more preferred embodiment, the improved property is a colour fading effect, i.e., a light yellow colour of the potato product.

In another more preferred embodiment, the improved property is an increased stiffness of the potato product.

In another more preferred embodiment, the improved property is a colour fading effect, i.e., a light yellow colour of the potato product.

In another more preferred embodiment, the improved property is a lower fat content of the potato product obtained from the enzyme-treated potato substance compared to the non-enzyme-treated potato substance.

The one or more exogenous enzymes may be any amyloglucosidase, glucose oxidase, laccase, lipase, maltogenic amylase, pectinase, pentosanase, protease, and transglutaminase, which provide an improved property to potato product.

The term "exogenous" means that the one or more enzymes are added to the potato substance to achieve a desirable property of the potato product. The term "exogenous" contrasts with enzymes that are naturally endogenous to potato or the result of recombinant expression of an enzyme gene present in the potato plant.

The term "amyloglucosidase" as used in the present invention is defined herein as a dextrin 6-alpha-D-glucanohydrolase which catalyses the endohydrolysis of 1,6-alpha-D-glucoside linkages at points of branching in chains of 1,4-linked alpha-D-glucose residues.

The term "glucose oxidase" as used in the present invention is defined herein as a beta-D-glucose:oxygen 1-oxidoreductase which catalyses the conversion of beta-D-glucose in the presence of mol;ecular oxygen to D-glucono-1, 5-lactone and hydrogen peroxide.

The term "laccase" as used in the present invention is defined herein as a benzenediol:oxygen oxidoreductase which catalyzes the conversion of four benzenediols in the presence of molecular oxygen to four benzosemiquinones and two waters.

The term "lipase" as used in the present invention is defined herein as a triacylglycerol acylhydrolase which catalyzes the hydrolysis of a triacylglycerol to diacylglycerol and a fatty acid anion.

The term "maltogenic amylase" as used in the present invention is defined herein as a 1,4- or 1,6-alpha-maltohydrolase which catalyses the removal of alpha-maltose from starch.

The term "pectinase" as used in the present invention is defined as any enzyme that degrades pectic substances. Pectic substances include homogalacturonans, xylogalacturonans, and rhamnogalacturonans as well as derivatives thereof. In the methods of the invention, the further pectinase treatment may be achieved by one or more pectinases, such as two or more pectinases of the same type (e.g., two different pectin methylesterases) or of different types (e.g., a pectin methylesterase and an arabinanase). The pectinase may, for example, be selected from the group consisting of arabinanase (catalyses the degradation of arabinan sidechains of pectic substances), arabinofuranosidase (removes arabinosyl substituents from arabinans and arabinogalactans), galactanase (catalyses the degradation of arabinogalactan and galactan sidechains of pectic substances), pectate lyase (cleaves glycosidic bonds in polygalacturonic acid by beta-elimination), pectin acetylesterase (catalyses the removal of acetyl groups from acetylated pectin), pectin lyase (cleaves the glycosidic bonds of highly methylated pectins by beta-elimination), pectin methylesterase (catalyses the removal of methanol from pectin, resulting in the formation of pectic acid, polygalacturonic acid), polygalacturonase (hydrolyses the glycosidic linkages in the polygalacturonic acid chain), rhamnogalacturonan acetylesterase (catalyses the removal of acetyl groups from acetylated rhamnogalacturonans), and rhamnogalacturonase and rhamnogalacturonan lyase (degrade rhamnogalacturonans).

The term "pentosanase" as used in the present invention is defined herein as a hydrolase which catalyses the cleavage of beta-1,4-linkages in pentosan.

The term "protease" as used in the present invention is defined herein as an enzyme which catalyses the hydrolysis of peptide linkages. It will be understood that the term "proteases" encompasses endoproteases and exopeptidases (aminopeptidases and carboxypeptidases).

The term "transglutaminase" as used in the present invention is defined herein as a protein-glutamine:amine gamma-glutamyltransferase which catalyses the conversion of a protein glutamine and an alkylamine to a protein $N^5$-alkylamine and ammonia.

In the methods of the present invention, any amyloglucosidase, glucose oxidase, laccase, lipase, maltogenic amylase, pectinase, pentosanase, protease, or transglutaminase may be used which possesses suitable enzyme activity in a pH and temperature range appropriate for making a potato product. It is preferable that the enzymes are active over broad pH and temperature ranges.

The term "effective amount" is defined herein as an amount of one or more enzymes that is sufficient for providing a measurable effect on at least one property of interest of the potato product.

In a preferred embodiment, the enzymes have a pH optimum in the range of about 3 to about 10. In a more preferred embodiment, the enzyme(s) has a pH optimum in the range of about 4.5 to about 8.5.

In another preferred embodiment, the enzymes have a temperature optimum in the range of about 5° C. to about 100° C. In a more preferred embodiment, the enzymes have a temperature optimum in the range of about 25° C. to about 75° C.

In the methods of the present invention, combinations of the enzymes selected from the group consisting of amyloglucosidase, glucose oxidase, laccase, lipase, maltogenic amylase, pectinase, pentosanase, protease, and transglutaminase may be used to improve one or more properties of the potato product.

In a preferred embodiment, the enzyme is an amyloglucosidase.

In a preferred embodiment, the enzyme is a glucose oxidase.

In a preferred embodiment, the enzyme is a laccase.

In a preferred embodiment, the enzyme is a lipase.

In a preferred embodiment, the enzyme is a maltogenic amylase.

In a preferred embodiment, the enzyme is a pentosanase.

In a preferred embodiment, the enzyme is a pectinase.

In another preferred embodiment, the enzyme is a protease.

In a preferred embodiment, the enzyme is a transglutaminase.

In a more preferred embodiment, the pectinase is an arabinofuranosidase.

In another more preferred embodiment, the pectinase is an arabinanase (catalyses the degradation of arabinan sidechains of pectic substances).

In another more preferred embodiment, the pectinase is a galactanase.

In another more preferred embodiment, the pectinase is a pectate lyase.

In another more preferred embodiment, the pectinase is a pectin acetylesterase.

In another more preferred embodiment, the pectinase is a pectin lyase.

In another more preferred embodiment, the pectinase is a pectin methylesterase.

In another more preferred embodiment, the pectinase is a polygalacturonase.

In another more preferred embodiment, the pectinase is a rhamnogalacturonan acetylesterase.

In another more preferred embodiment, the pectinase is a rhamnogalacturonase.

In another more preferred embodiment, the pectinase is a rhamnogalacturonan lyase.

The source of the enzymes is not critical for use in the methods of the present invention for improving one or more properties of a potato product. Accordingly, the enzymes may be obtained from any source such as a plant, microorganism, or animal. The enzymes are preferably obtained from a microbial source, such as a bacterium or a fungus, e.g., a filamentous fungus or yeast.

In a preferred embodiment, the enzymes are obtained from a bacterial source. For example, the enzymes may be obtained from an *Acetobacter, Acinetobacter, Agrobacterium, Alcaligenes, Arthrobacter, Azotobacter, Bacillus, Comamonas, Clostridium, Gluconobacter, Halobacterium, Mycobacterium, Rhizobium, Salmonella, Serratia, Streptomyces, E. coli, Pseudomonas, Wolinella*, or methylotrophic bacterium strain.

In a more preferred embodiment, the enzymes are obtained from an *Acetobacter aceti, Alcaligenes faecalis, Arthrobacter oxidans, Azotobacter vinelandii, Bacillus alkalophilus, Bacillus amyloliquefaciens, Bacillus anitratum, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis, Bacillus thuringiensis, Comamonas testosteroni, Clostridum tyrobutyricum, Gluconobacter dioxyaceticus, Gluconobacter liquefaciens, Gluconobacter suboxydans, Halobacterium cutirubrum, Mycobacterium convolutum, Rhizobium melioti, Salmonella typhimurium, Serratia marcescens, Streptomyces lividans, Streptomyces murinus, Pseudomonas aeruginosa, Pseudomonas fluorescens, Pseudomonas putida*, or *Wolinella succinogens* strain.

In another preferred embodiment, the enzymes are obtained from a fungal source. For example, the enzymes may be obtained from a yeast strain such as a *Candida, Kluyveromyces, Pichia, Saccharomyces, Schizosaccharomyces*, or *Yarrowia* strain; or from a filamentous fungal strain such as an *Acremonium, Aspergillus, Aureobasidium, Chrysosporium, Cryptococcus, Filibasidium, Fusarium, Humicola, Magnaporthe, Monilia, Mucor, Myceliophthora, Neocallimastix, Neurospora, Paecilomyces, Penicillium, Phanerochaete, Piromyces, Schizophyllum, Sclerotium, Sporotrichum, Talaromyces, Thermoascus, Thielavia, Tolypocladium*, or *Trichoderma* strain.

In another more preferred embodiment, the enzymes are obtained from a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* strain.

In another more preferred embodiment, the enzymes are obtained from an *Aspergillus aculeatus, Aspergillus awamori, Aspergillus foetidus, Aspergillus japonicus, Aspergillus nidulans, Aspergillus niger, Aspergillus oryzae, Chrysosporium lignorum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides, Fusarium venenatum, Humicola insolens, Humicola lanuginosa, Monilia sitophila, Mucor miehei, Myceliophthora thermophila, Neurospora crassa, Penicillium pur-*

*purogenum, Phanerochaete chrysporum, Polyporus pinsitus, Polyporus versicolour, Sclerotium rolfsii, Sporotrichum thermophile, Trichoderma citrinoviride, Trichoderma hamatum, Trichoderma harzianum, Trichoderma koningii, Trichoderma longibrachiatum, Trichoderma polysporum, Trichoderma reesei, Trichoderma saturnisporum,* or *Trichoderma viride* strain.

The enzymes may be obtained from the organism in question by any suitable technique, and in particular by use of recombinant DNA techniques known in the art (c.f. Sambrook, J. et al., 1989, *Molecular Cloning, A Laboratory Manual,* Cold Spring Harbor Press, Cold Spring Harbor, N.Y., USA). The use of recombinant DNA techniques generally comprises cultivation of a host cell transformed with a recombinant DNA vector, consisting of the product gene of interest inserted between an appropriate promoter and terminator, in a culture medium under conditions permitting the expression of the enzyme and recovering the enzyme from the culture. The DNA sequence may be of genomic, cDNA or synthetic origin or any mixture of these, and may be isolated or synthesized in accordance with methods known in the art. The enzyme may also be obtained from its naturally occurring source, such as a plant or organism, or relevant part thereof.

In the methods of the present invention, the enzymes may be obtained from commercial suppliers. A commercially available amyloglucosidase is AMG™ (an *Aspergillus niger* amyloglucosidase, available from Novo Nordisk A/S, Denmark). A commercially available glucose oxidase is GLUZYME™ (an *Aspergillus niger* glucose oxidase, available from Novo Nordisk A/S, Denmark). Commercially available laccases are NS51001 (a *Polyporus pinsitius* laccase, available from Novo Nordisk A/S, Denmark) and NS51002 (a *Myceliopthora thermophila* laccase, available from Novo Nordisk A/S, Denmark). A commercially available lipase is NOVOZYM® 677 BG (a *Thermomyces lanuginosus* lipase, available from Novo Nordisk A/S, Denmark). A commercially available maltogenic amylase is NOVAMYL™ (a *Bacillus stearothermophilus* maltogenic amylase, available from Novo Nordisk A/S, Denmark). Commercially available pectinases useful in the present invention are NovoShape™ (a *Bacillus* rhamnogalacturonase and rhamnogalacturonan lyase, available from Novo Nordisk A/S, Denmark), PECTINEX™ Ultra (an *Aspergillus niger* pectinase, available from Novo Nordisk A/S, Denmark), and PEELZYM™ (an *Aspergillus niger* preparation containing pectinases, hemicellulases, cellulases, and arbinases, available from Novo Nordisk A/S, Denmark). Commercially available pentosanases are PENTOPAN™ (a *Humicola insolens* pentosanase, available from Novo Nordisk A/S, Denmark) and PENTOPAN™ MONO (a *Thermomyces lanuginosus* pentosanase, available from Novo Nordisk A/S, Denmark). Commercially available proteases are ALCALASE (a *Bacillus licheniformis* protease, available from Novo Nordisk A/S, Denmark), GLUTENASE™ (a *Bacillus amyloliquefaciens* neutral protease, available from Novo Nordisk A/S, Denmark), NEUTRASE™ (a *Bacillus amyloliquefaciens* endoprotease, available from Novo Nordisk A/S, Denmark), and SAVINASE® (a *Bacillus* protease, available from Novo Nordisk A/S, Denmark). A commercially available transglutaminases ia ACTIVA™ (a *Streptoverticillium mobaraense* transglutaminase, available from Ajinomoto, Japan).

In the methods of the present invention, the potato substance may be further treated with an alpha-amylase during the enzyme-treatment step (see, for example, U.S. Pat. No. 4,058,631.

The term "alpha-amylase" as used in the present invention is defined herein as a 1,4-alpha-D-glucan glucanohydrolase which catalyses the conversion of polysaccharide containing alpha-(1-4)-linked glucose units in the presence of water to maltooligosaccharides.

The alpha-amylase may be of any origin, including mammalian and plant, and preferably of microbial (bacterial, yeast or fungal) origin and may be obtained by techniques conventionally used in the art, as described earlier.

Commercially available amylases useful in the present invention are FUNGAMYL® (an *Aspergillus oryzae* alpha-amylase, available from Novo Nordisk A/S, Denmark), BAN™ (a *Bacillus licheniformis* alpha-amylase, available from Novo Nordisk A/S, Denmark), TERMAMYL® (a *Bacillus* alpha-amylase, available from Novo Nordisk A/S, Denmark), and THERMOZYME™, a *Bacillus* alpha-amylase, available from Novo Nordisk A/S, Denmark). Other useful commercially available amylase products include GRINDAMYL™ A 1000 or A 5000 (available from Grindsted Products, Denmark) and AMYLASE H or AMYLASE P (available from Gist-Brocades, The Netherlands).

In the methods of the present invention, the potato substance may be further treated with a pectinase during the enzyme-treatment step.

In terms of enzyme activity, the appropriate dosage of a given enzyme for improving a specific property or properties of a potato product as described earlier will depend on the enzyme in question. The skilled person may determine a suitable enzyme unit dosage on the basis of methods known in the art.

The treatment of the potato substance with the one or more enzymes necessarily involves contacting the potato substance with the enzyme(s) under conditions suitable to provide the improved property or properties as described herein. Accordingly, the enzyme treatment may be performed by contacting the potato substance with the one or more enzymes in an aqueous preparation, e.g., an aqueous solution or aqueous slurry. The aqueous enzyme preparation may comprise a single enzyme component, e.g., a mono-component enzyme preparation, or a mixture of two or more of enzymes. The enzyme treatment can be performed by immersing or dipping the potato substance in such an aqueous preparation. The potato substance may also be enzyme-treated by coating the potato substance with, for example, spray equipment.

The enzyme treatment of the potato substance is performed for a period of time sufficient to provide the improved property or properties of the potato product. The potato substance is preferably treated for a period of time of at least 5 minutes, more preferably at least 10 minutes, even more preferably at least 20 minutes, and most preferably at least 30 minutes.

In the case where the potato substance is a dough or batter, the one or more enzymes may be incorporated into the substance by mixing using methods well known in the art.

Thus, the enzymes to be used in the methods of the present invention may be in any form suitable for the use in question, e.g., in the form of a dry powder, agglomerated powder, or granulate, in particular a non-dusting granulate, a liquid, in particular a stabilized liquid, or a protected enzyme. Granulates and agglomerated powders may be prepared by conventional methods, e.g., by spraying the enzyme(s) onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy. The enzymes may be contained in slow-release formulations. Methods for preparing slow-release formulations are well known in the art. Liquid enzyme preparations may, for instance, be stabilized by adding nutritionally acceptable stabilizers such as a sugar, a sugar alcohol or another polyol, and/or lactic acid or another organic acid according to established methods.

In the methods of the present invention, the effective amount of the enzyme(s) is about 0.01 mg to about 100 mg per kilogram of potato substance, more preferably about 0.1 mg to about 25 mg per kilogram of potato substance, even more preferably about 0.5 mg to about 5 mg per kilogram of potato substance, and most preferably about 1 mg to about 5 mg per kilogram of potato substance.

In the methods of the present invention, the processing step may be accomplished by any method known in the art for producing a potato product. The processing step may involve such methods as, but not limited to, frying in oil and baking to prepare the enzyme-treated potato substance for consumption. Alternatively, the processing step may result in a frozen potato product that requires frying or baking to become consumable. It will be understood that the potato substance may be prepared for consumption by other conventional procedures such as microwave heating or any other method that is used for cooking potato products.

Any of the conventional frying fats and oils may be used for frying the enzyme-treated potato substance in accordance with the invention. Such fats and oils include, but are not limited to, animal, vegetable and marine fats and oils, such as, e.g., lard, tallow, cottonseed oil, corn oil, soy bean oil, coconut oil, palm oil, whale oil, partially hydrogenated fats and oils and similar such as glycerides having from, e.g., about 12 to about 22 carbon atoms in the molecule.

The methods of the present invention further comprise the step of blanching the potato substance. Preferably, the blanching is performed prior to treatment of the potato substance with enzyme. In one embodiment of the invention, the method comprises the steps of (i) blanching the potato substance; and (ii) treating the blanched potato substance with one or more enzymes selected from the group consisting of amyloglucosidase, glucose oxidase, laccase, lipase, maltogenic amylase, pectinase, pentosanase, protease, and transglutaminase. The blanching may be performed in accordance with procedures well-known in the art (see, for example, U.S. Pat. No. 4,254,153 and Andersson et al., 1994, *Critical Reviews in Food Science and Nutrition* 34: 229–251). The blanching may, for example, be performed by heating the potato substance in an aqueous solution, such as pure water, preferably in the temperature range of about 70° C. to about 100° C. for about 2 to about 15 minutes, more preferably in the temperature range of about 75° C. to about 90° C. for about 4 to about 10 minutes, and most preferably at about 75° C. for about 10 minutes. Alternatively, the potato substance may be blanched in steam, such as at atmospheric pressure for about 2 to about 10 minutes. Moreover, the enzyme treatment may be performed concurrently with the blanching step.

In another embodiment, the blanched potato substance, after enzyme treatment and prior to dehydration, is immersed in a dilute aqueous solution containing a food grade sequestering agent, such as sodium acid pyrophosphate (SAPP) and a reducing sugar, such as dextrose or glucose. SAPP, present at a level of e.g., about 0.5% to 1.5%, may minimize product discolouration by chelating metal ions such as iron and copper present in the processing water. Dextrose or other reducing sugar in the aqueous solution facilitates uniform colour development upon frying.

The methods of the present invention may further comprise the step of parfrying the enzyme-treated potato substance. The partially dehydrated potato substance may be parfried by immersion in a deep fat fryer for a short period of time, for example, 20 to 240 seconds at a fat temperature of about 150° C.–220° C. After par-frying, the potato substance may be frozen, packaged and shipped or stored for subsequent use. To prepare the parfried potato substance for consumption, the potato substance is fried in a deep fat or oil bath, for example, at a temperature of from about 150° C. to 220° C. for 1 to 10 minutes to develop colour and crispiness.

The methods of the present invention may further comprise the step of freezing the enzyme-treated potato substance, which may or may not have been parfried before freezing. Any conventional method known in the art for potato products may be used.

The potato substance may be treated with enzyme in accordance with the present invention and frozen without being par-fried. Thus, potato pieces may be blanched and contacted with an aqueous solution containing one or more enzymes as described earlier. After contact with the aqueous solution the potato substance preferably is partially dehydrated, to effect a weight loss of e.g., between 5% to 25%, after which the potato substance is frozen. To reconstitute the frozen potato substance for consumption, the potato substance is fried, for example, in a deep fat or oil bath at a temperature in the range of about 150° C. to about 220° C. Where the potato substance is frozen, but not par-fried before being frozen, the potato substance has a higher moisture content than the par-fried material, and consequently requires a slightly longer frying period of time, typically 4 to 10 minutes or between about 4 to 8 minutes. The specific time-temperature conditions for frying the frozen potato substance for consumption are typically a function of the size of the potato substance, and can be readily determined by those skilled in the art.

In another embodiment, the potato substance is partially dried after the enzyme treatment, such as by drying in hot air at 100–300° C. for 5–20 minutes. Thus, after the enzyme treatment, but before frying or baking, the potato substance may be drained and partly dehydrated to reduce the moisture content. Any of the conventional drying procedures used in the production of potato products, including French fries, may be used such as subjecting the potato substance to heated air having a temperature in the range of from about 40° C. to about 200° C. for about 2 to about 20 minutes in order to reduce the moisture content of the potato substance by about 5% to 30% of their initial weight.

In another embodiment of the invention, the drying step is followed by a "resting step" in which the potato substance is cooled down by standing at a lower temperature, such as at ambient temperature, for a sufficient period of time. The potato substance may be cooled to at least about 40° C. before being fried. The resting step may consist of incubating the potato substance at ambient temperature for about 5–10 minutes.

In another embodiment of the present invention, the methods for producing a consumable potato product comprise: (a) blanching a potato substance; (b) treating the blanched potato substance with one or more enzymes selected from the group consisting of an amyloglucosidase, glucose oxidase, laccase, lipase, maltogenic amylase, pectinase, pentosanase, protease, and transglutaminase; and (c) parfrying or deep frying the enzyme-treated potato substance; with optional freezing the potato after step (c).

In another embodiment, the methods of the invention may further comprise the step of coating the potato pieces before, during and/or after the enzyme treatment. The treatment of the surface of the potato pieces after the coating is particularly relevant in cases where a pectin-containing coating has been used. The coating may be any coating found suitable, such as e.g., a hydrocolloid coating and/or a starch-based coating. The coating may be performed by any coating techniques known in the art. The coating may comprise pectic substances. The coating material may have been subjected to a treatment with pectin methyl enzyme or another pectinase as described herein.

The present invention also relates to methods for producing a consumable potato product comprising: (a) blanching potato pieces; (b) treating the blanched potato pieces with one or more enzymes selected from the group consisting of an amyloglucosidase, glucose oxidase, laccase, lipase, maltogenic amylase, pectinase, pentosanase, protease, and transglutaminase; (c) parfrying the enzyme treated potato; (d) freezing the potato pieces after step (c); and (e) frying or baking the potato product for consumption.

The present invention also relates to methods for producing French fries, comprising: (a) treating potato pieces with one or more enzymes selected from the group consisting of an amyloglucosidase, glucose oxidase, laccase, lipase, maltogenic amylase, pectinase, pentosanase, protease, and transglutaminase; and (b) frying or baking the enzyme-treated potato pieces to obtain French fries ready for consumption. The enzyme-treated potato pieces may be parfried and/or frozen before step (b).

The present invention also relates to methods for producing potato chips, comprising: (a) treating potato slices with one or more enzymes selected from the group consisting of an amyloglucosidase, glucose oxidase, laccase, lipase, maltogenic amylase, pectinase, pentosanase, protease, and transglutaminase; and (b) frying or baking the enzyme-treated potato slices to obtain potato chips ready for consumption. The enzyme-treated potato slices may be parfried and/or frozen before step (b).

The present invention also relates to methods for producing a consumable potato product, comprising: (a) treating a potato batter or a potato dough with one or more enzymes selected from the group consisting of an amyloglucosidase, glucose oxidase, laccase, lipase, maltogenic amylase, pectinase, pentosanase, protease, and transglutaminase; and (b) frying or baking the enzyme-treated potato batter or potato for consumption.

It is understood that any of the embodiments described herein may be combined to produce a potato product.

The invention also relates to potato products obtained by the methods of the present invention. The potato product, having improved properties as compared to a similar method without the treatment with enzyme. Accordingly, by the present invention is provided a potato product, wherein the crispiness of the resulting potato product ready for consumption is increased compared to a similar method without the treatment with enzyme. Furthermore, it is contemplated that the consumable resulting potato product remains crispy for an extended period of time compared to a potato product not treated with enzyme.

The present invention is further described by the following examples that should not be construed as limiting the scope of the invention.

EXAMPLES

Enzymes

FUNGAMYL™ 2500 BG (*Aspergillus oryzae* α-amylase, 2500 FAU/g), GLUTENASE™ 5.0 BG (*Bacillus subtilis* neutral protease, 5 AU/g), GLUZYME™ 500 MG (*Aspergillus oryzae* glucose oxidase, 500 GODU/g), NOVAMYL™ 1500 MG (*Bacillus stearothermophilus* maltogenic amylase, 1500 MANU/g), NOVOZYM™ 384 (*Thermomyces lanuginosus* pentosanase) (1000 NCU/g), PECTINEX™ Ultra (*Aspergillus niger* pectinase, 26000 PG/ml), and *Streptomyces lydicus* transglutaminase (TGase) (190 U/g) were obtained from Novo Nordisk Biochem North America, Franklinton, N.C.

LIPOLASE™ (*Trichoderma lanuginosus* lipase) (105 KLU/g) and *Polyporus pinsitus* laccase (PpL) (1,900 LACU/ml) were obtained from Novo Nordisk A/S, Bagsvaerd, Denmark. The *Thielavia terrestris* glucoamylase was obtained from Novo Nordisk Biotech, Inc., Davis, Calif.

The *Microdochium nivale* carbohydrate oxidase was isolated as described in WO 99/31990.

Example 1

Enzyme Treatment of Potatoes

Potatoes (Russet, 1.07 density, of 400–500 g/tuber) were manually peeled and cut into sticks of approximately 0.8×0 to 0.8×7.6 cm size each weighing approximately 5 g. The potato sticks were then rinsed, wiped with a paper towel, and soaked with or without enzyme in a 500-ml glass beaker containing 300 ml of distilled water under magnetic stirring (300 rpm) for approximately 17 hours at 23° C.

Two series of enzyme treatments (A and B) were performed. In series A, five groups containing 20 potato sticks (148–166 g) each were treated individually with NOVAMYL™, FUNGAMYL™, *T. terrestris* glucoamylase, and carbohydrate oxidase. For series B, eight groups containing 11 sticks (83–102 g) each were treated individually with GLUTENASE™, GLUZYME™, LIPOLASE™, NOVOZYM 384, PECTINEX™, laccase, and *T. terrestris* glucoamylase. A no enzyme treatment was run as a control for each series. GLUTENASE™, LIPOLASE™, NOVAMYL™, PECTINEX™, glucoamylase, transglutaminase, and carbohydrate oxidase were dosed at 0.02, 210, 0.1, 0.2, 20, 0.4, or 0.7 of their respective units per gram of potato, respectively, and all other enzymes were dosed at 2 of their respective units per gram. For the commercial enzyme preparations, the doses corresponded to the higher end of recommended dosages for their commercial applications (on juice, starch, or bread). The dosage of *T. terrestris* glucoamylase was based on that of AMG™ (*Aspergillus niger* glucoamylase) for baking.

Frying of the potato sticks was performed at 170° C. in a cylindric aluminum pan (21 cm inner-diameter and 14 cm height) containing 3.2 liters of vegetable shortening (all-vegetable, partially hydrogenated soybean/cotton seed oil with mono/di-glycerides) under magnetic stirring. The temperature was monitored using a Hewlett-Packard Multimeter E2377A. During frying, 5–9 sticks were placed in a "box sieve" of 1.5×13×7.5 cm size, made from an aluminum door screen (ACE, Brite Aluminum, hole size: 1.5×2.0 mm), to ensure complete immersion. Each frying round led to a 1–2° C. temperature drop of the shortening, which was reheated to 170° C. before the next round of frying.

For series A, nine sticks from each group were first partially fried (see below) before being fully fried for 2 minutes, whereas five and six sticks from each group were fried for 3 and 4 minutes, respectively, in two rounds of frying. For series B, five and six sticks from each group were fried for 3 minutes in two rounds of frying. For sticks not treated with enzyme, a longer frying time of approximately 10 minutes was needed to make satisfactory French Fries. However, the selected time allowed the detection of enzymatic effects.

Partial frying was accomplished by immersing five box sieves holding nine potato sticks each into vegetable shortening heated to 170° C. Upon immersion into the oil, the frying temperature dropped to 125° C. After 2.5 minutes, the partially fried fries were drained of the oil with a sieve and cooled to 23° C. for 16 hours before final frying (at 170° C.).

Example 2

Characterization of Fried Potato Sticks After Enzyme Treatment

The fried potato sticks were rated visually for colour, appearance, and stiffness. Anresco of San Francisco determined the fat content of the fried fries.

When fried fries from series A (with or without the partial frying) were compared, it was evident that carbohydrate oxidase treatment led to fries with more pronounced golden colour and crispiness than the untreated control. Fries treated with NOVAMYL™, FUNGAMYL™, and *T. terrestris* glucoamylase showed less significant colour increase relative to the no enzyme treatment control.

When unfried sticks from series B were compared, significant alteration of the appearance was observed with potato sticks treated with GLUZYME™ and PECTINEX™. PECTINEX™ resulted in a reddening of the sticks, in contrast to the yellow colour of the control. GLUZYME™ resulted in a red colouring and a rugged surface, indicating significant modification and degradation of the surface structure of sticks.

When fried fries from series B were compared, the GLUZYME™ and PECTINEX™ treatments led to fries with a pronounced golden colour, crispiness, stiffness, and rugged/"pebbled" surface than the untreated control. Fries treated with GLUTENASE™ showed less golden colour, but more stiffness than the control. The effect of treatment with Novozym 384, *P. pinsitius* laccase, LIPOLASE™, and transglutaminase was insignificant relative to the no enzyme treatment control.

In terms of fat retention in Series A, fries pretreated with NOVAMYL™ and FUNGAMYL™ possessed a 17 or 15% higher fat content than the control, respectively, while fries pretreated with glucoamylase or carbohydrate oxidase possessed 18 or 8% less fat, respectively (Table 1). In terms of fat retention for Series B, fries pretreated with NOVOZYM 384, GLUTENASE™, PECTINEX™, *P. pinsitus* laccase, LIPOLASE™, and transglutaminase contained 35, 22, 24, 25, 14, or 14% less fat than the control, respectively, while treatment with GLUZYME™ led to 21% higher fat retention (Table 1)

TABLE 1

Effect of enzyme on the fat content (w/w, % ± standard deviation) of fried fries

| Series A | | Series B | |
|---|---|---|---|
| None | 6.15 ± 0.3 | None | 4.20 ± 0.01 |
| NOVAMYL | 7.21 ± 0.11 | N384 | 2.72 ± 0.06 |
| FUNGAMYL | 7.05 ± 0.01 | GLUTENASE | 3.27 ± 0.01 |
| Glucoamylase | 5.02 ± 0.10 | PECTINEX | 3.21 ± 0.01 |
| Carbohydrate Oxidase | 5.67 ± 0.23 | GLUZYME | 5.09 ± 0.01 |
| | | Laccase | 3.14 ± 0.42 |
| | | LIPOLASE | 3.62 ± 0.23 |
| | | Transglutaminase | 3.62 ± 0.01 |

The stiffness/strength of the fried potato sticks was determined by holding each stick at ⅙ of its length, and measuring the angle of the remaining ⅚ part of the potato stick. For GLUZYME™, PECTINEX™, or GLUTENASE™-treated fries, the angle was approximately 10, 10, or 20°, in contrast to the approximately 44–55° angle found with untreated fries. Treatment with these enzymes led to stronger coat of the fried potato sticks than the no enzyme treated sticks.

The most significant effects observed with the enzymes tested are summarized in Table 2.

TABLE 2

Enzymatic effects on fries

| Enzyme type | Color | Strength | Rugged coat | Fat |
|---|---|---|---|---|
| Oxidative | + | + | + | mix |
| Pectinolytic | + | + | + | — |
| Amylolytic | Insignificant | Insignificant | Insignificant | mix |
| Lipolytic | Insignificant | Insignificant | Insignificant | — |
| Cellulolytic | Insignificant | Insignificant | Insignificant | — |
| Proteolytic | − | + | Insignificant | — |

The apparent coat-strengthening and colour-enhancing effect from carbohydrate oxidase and GLUZYME™ was probably related to their action on starch. These enzymes oxidize mono-, di- or oligomeric carbohydrates and concomitantly generate hydrogen peroxide (from $O_2$). Both the starch oxidation and hydrogen peroxide might contribute to the observed structural degradation on sticks before frying as well as the enhanced crispiness or strength of fried fries.

The apparent coat-strengthening and colour-fading effects from GLUTENASE™ was probably related to its action on the proteinaceous components of potato. Degradation of potato protein might lead to less colour-generating Maillard reaction during frying. Although such decrease in golden appearance might not be desirable for French Fries, it would be beneficial for potato chips or other potato foods.

Example 3

Pectin Methylesterase Treatment of French Fries

Two kilograms of Bintje potatoes were peeled and cut into 10 mm×10 mm elongated strips by use of a kitchen french fry cutter (Westmark küchenhelfer). The cut potatoes were blanched in batches of 500 g of potato in 1500 ml of water at 75° C. for 10 minutes.

Then 400 g of the blanched potato pieces were immersed in 1000 ml of enzyme solution for 1 hour at 25° C. The enzyme solution was composed of 5 g of NovoShape™ (Novo Nordisk A/S) and 1000 ml of a 0.25 mM $CaCl_2$ solution. NovoShape™ (Novozymes A/S, Bagsvaerd, Denmark) is a monocomponent pectin methylesterase enzyme product derived from *Aspergillus aculeatus*. NovoShape™ has an activity of 10 PEU/g. One PEU is defined as the enzyme activity which produces one millimole acid equivalents per minute from methylated pectin at standard incubation conditions in a titrator. The standard conditions were 0.48% citrus pectin substrate solution, pH 4.8, 30.0° C., and 2 minutes reaction time. The 0.48% citrus pectin substrate solution was citrus pectin from Copenhagen Pectin, Denmark, with % DE 69.2, % AGU 79.6, MW 10,200 and 89.72% dry matter, dissolved in 10 mM $MgCl_2$, adjusted to pH 4.8. The amount of millimole acid equivalents produced by the enzyme was determined using 0.050 N NaOH as the titrant. Another 400 g of the blanched potatoes were immersed in 1000 ml of 0.25 mM $CaCl_2$ solution for 1 hour at 25° C.

Next, the potato pieces were drained and placed in an oven at 130° C. for 7 minutes to dry. After drying, the potato pieces rested at room temperature for 8 minutes before frying for 2 minutes in 195° C. corn oil in a deep fryer from DANKOK, Model ELT 8B. The par-fried and drained potato pieces were frozen at −18° C.

The frozen potato pieces were fried for approximately 5 minutes at 195° C. in corn oil in a deep fryer from DANKOK, Model ELT 8B until satisfactory colour was obtained. The two batches of differently treated potato pieces (with and without pectin methylesterase) were fried simultaneously in two different nets immersed in the deep fryer.

Immediately after frying the two different batches of french fries were served to 13 persons who were asked to indicate which of the two samples (with random numbering) was the most crispy. Nine out of the 13 persons chose the pectin methylesterase treated french fries as being most crispy.

These results show that pectin methylesterase, when added to potato pieces, increased the crispiness of the potato pieces after deep frying.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for producing a consumable product from potatoes, comprising:
    (a) treating a peeled, cut potato substance with an effective amount of one or more exogenous enzymes selected from the group consisting of a glucose oxidase, laccase, lipase, pentosanase, and transglutaminase, and
    (b) processing the enzyme-treated potato substance to produce a potato product.

2. The method of claim 1, wherein the potato substance is obtained from Bintje, Russet Burbank, Kennebec, Norchip, Atlantic, Shepody, Sebago, Red Pontiac, Red Warba, Irish Cobbler "BC", Norgold Russet "BC", Norland, Atlantic, White Rose, Superior, Centennial Russet, Keswick "NB 1", and Green Mountain.

3. The method of claim 1, wherein the potato substance is selected from the group consisting of raw potato, potato dough, and potato batter.

4. The method of claim 1, further comprising blanching the potato substance prior to the enzymatic treatment.

5. The method of claim 1, further comprising blanching the potato substance concurrently with the enzyme treatment step.

6. The method of claim 1, further comprising partially drying the potato substance after the enzymatic treatment.

7. The method of claim 1, further comprising parfrying the enzyme-treated potato substance before processing to produce the potato product.

8. The method of claim 1, further comprising freezing the enzyme-treated potato substance before processing to produce the potato product.

9. The method of claim 1, further comprising coating the potato substance.

10. The method of claim 9, wherein the coating is a hydrocolloid coating and/or a starch-based coating.

11. The method of claim 1, further comprising treating the potato substance with a starch degrading enzyme during the enzyme-treatment step.

12. The method of claim 11, wherein the starch degrading enzyme is an alpha-amylase.

13. The method of claim 1, wherein the processing of the enzyme-treated potato substance comprises baking, frying, or microwaving.

14. The method of claim 1, wherein the potato product is fried.

15. The method of claim 1, wherein the potato product is baked.

16. The method of claim 1, wherein the potato product is frozen.

17. The method of claim 16, wherein the frozen potato product has been parfried before freezing.

18. The method of claim 1, wherein the potato product resulting from enzyme-treatment has an improved property selected from the group consisting of an increased crispiness, enhanced colour, faded colour, increased stiffness, rugged surface, improved flavour and lower fat content, compared to a potato product obtained without enzyme treatment.

19. The method of claim 1, wherein the effective amount of the enzyme is about 0.01 mg to about 100 mg per kilogram of potato substance.

20. The method of claim 19, wherein the effective amount of the enzyme is about 0.1 mg to about 25 mg per kilogram of potato substance.

21. The method of claim 20, wherein the effective amount of the enzyme is about 0.5 mg to about 5 mg per kilogram of potato substance.

22. The method of claim 21, wherein the effective amount of the enzyme is about 1 mg to about 5 mg per kilogram of potato substance.

* * * * *